United States Patent
Sorenson et al.

(10) Patent No.: US 6,712,922 B2
(45) Date of Patent: Mar. 30, 2004

(54) METHOD OF FABRICATING A MULTIPLE COMPONENT WEB

(75) Inventors: Jesse Paul Sorenson, Little Chute, WI (US); Donald Joseph Sanders, Larsen, WI (US); Paul William Christoffel, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 383 days.

(21) Appl. No.: 09/834,870

(22) Filed: Apr. 13, 2001

(65) Prior Publication Data

US 2002/0157778 A1 Oct. 31, 2002

(51) Int. Cl.$^7$ ................................................. A61F 13/15
(52) U.S. Cl. ................. 156/164; 156/160; 156/161; 156/163; 156/229; 156/250; 156/73.1
(58) Field of Search ................................. 156/160, 161, 156/163, 164, 229, 250, 72.1

(56) References Cited

U.S. PATENT DOCUMENTS

| | | | | |
|---|---|---|---|---|
| 5,399,219 A | * | 3/1995 | Roessler et al. | 156/259 |
| 5,484,505 A | | 1/1996 | Isakson et al. | 156/470 |
| 5,484,645 A | | 1/1996 | Lickfield et al. | 428/198 |
| 5,527,304 A | | 6/1996 | Buell et al. | 604/385.2 |
| 5,540,796 A | | 6/1996 | Fries | 156/164 |
| 5,578,152 A | | 11/1996 | Goulait et al. | 156/66 |
| 5,622,581 A | * | 4/1997 | Ducker et al. | 156/163 |
| 5,669,996 A | * | 9/1997 | Jessup | 156/85 |
| 5,702,551 A | | 12/1997 | Huber et al. | 156/73.1 |
| 5,705,013 A | | 1/1998 | Nease et al. | 156/260 |
| 5,706,524 A | * | 1/1998 | Herrin et al. | 2/400 |
| 5,827,260 A | | 10/1998 | Suzuki et al. | 604/385.2 |
| 5,858,292 A | | 1/1999 | Dragoo et al. | 264/115 |
| 5,858,515 A | | 1/1999 | Stokes et al. | 428/195 |
| 5,916,203 A | | 6/1999 | Brandon et al. | 604/367 |
| 6,022,432 A | | 2/2000 | Elsberg et al. | 156/73.1 |
| 6,036,805 A | | 3/2000 | McNichols | 156/227 |
| 6,113,717 A | | 9/2000 | Vogt et al. | 156/73.1 |
| 6,124,001 A | | 9/2000 | Sugita et al. | 427/538 |
| 6,375,646 B1 | | 4/2002 | Widlund et al. | 604/385.3 |
| 2002/0045879 A1 | | 4/2002 | Karami | 604/391 |

FOREIGN PATENT DOCUMENTS

| | | | | |
|---|---|---|---|---|
| CA | 2096672 | | 11/1997 | A61F 13/56 |
| EP | 0809992 A1 | | 12/1997 | A61F 13/62 |
| GB | 2308290 A | | 6/1997 | A61F 13/15 |
| JP | 03176053 | | 7/1991 | A61F 13/15 |
| JP | 2000-26015 A | * | 1/2000 | |
| WO | WO 91/04724 | | 4/1991 | A61F 13/56 |
| WO | WO 98/18421 | | 5/1998 | A61F 13/15 |
| WO | WO 00/20208 | | 4/2000 | B32B 27/02 |
| WO | WO 00/37009 | | 6/2000 | A61F 13/15 |
| WO | WO 01/82852 | | 11/2001 | A61F 13/15 |
| WO | WO 02/41816 | | 5/2002 | A61F 13/00 |

OTHER PUBLICATIONS

US 5,915,536, 6/1999, Alberts et al. (withdrawn)

* cited by examiner

*Primary Examiner*—Jeff H. Aftergut
(74) *Attorney, Agent, or Firm*—Dority & Manning, P.A.

(57) ABSTRACT

Methods and apparatus for assembly of extensible composite webs and web sausages, and personal care articles manufactured from such webs. The invention comprises fabricating a resiliently extensible web by bringing together and securing to each other as discrete elements, intervening web substrate elements between resiliently stretchable elastic elements. Securement between elastic elements and web substrate elements is defined by alternating zones of securement and non-securement along a length of the web substrate. The invention comprises deactivating elastic elements in the non-securement zones thereby to retract elastic strands in the non-securement zones without retracting the corresponding web or webs in such non-securement zones, and correspondingly, to distinguish the securement zones as relatively more resiliently stretchable and the non-securement zones as relatively less resiliently stretchable. The invention further comprises applying, to the relatively non-stretchable non-securement zones, fastener material extending generally between adjacent ones of the relatively more resiliently stretchable securement zones.

8 Claims, 6 Drawing Sheets

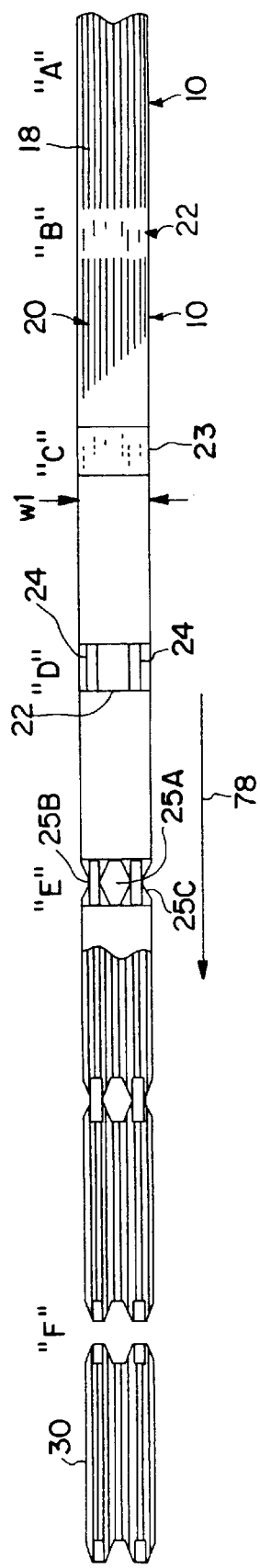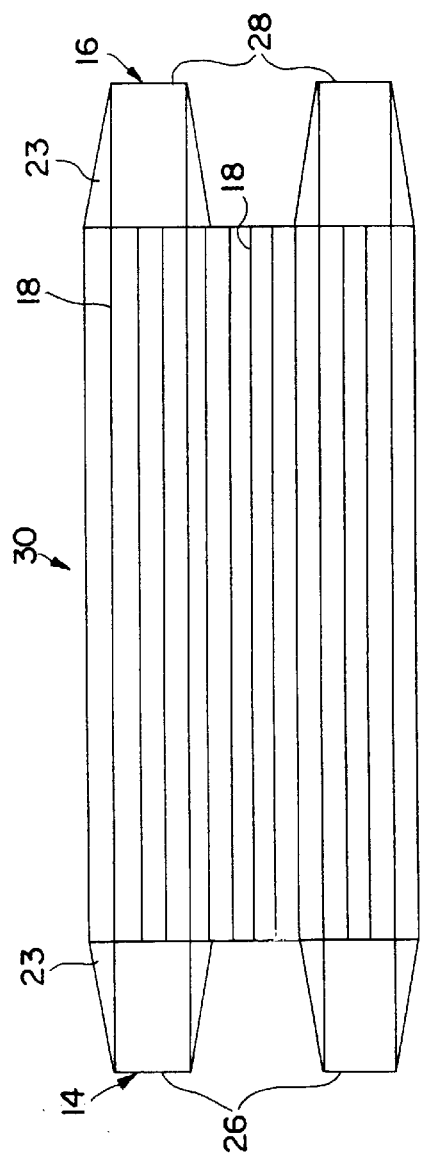
FIG. 1A
FIG. 1B

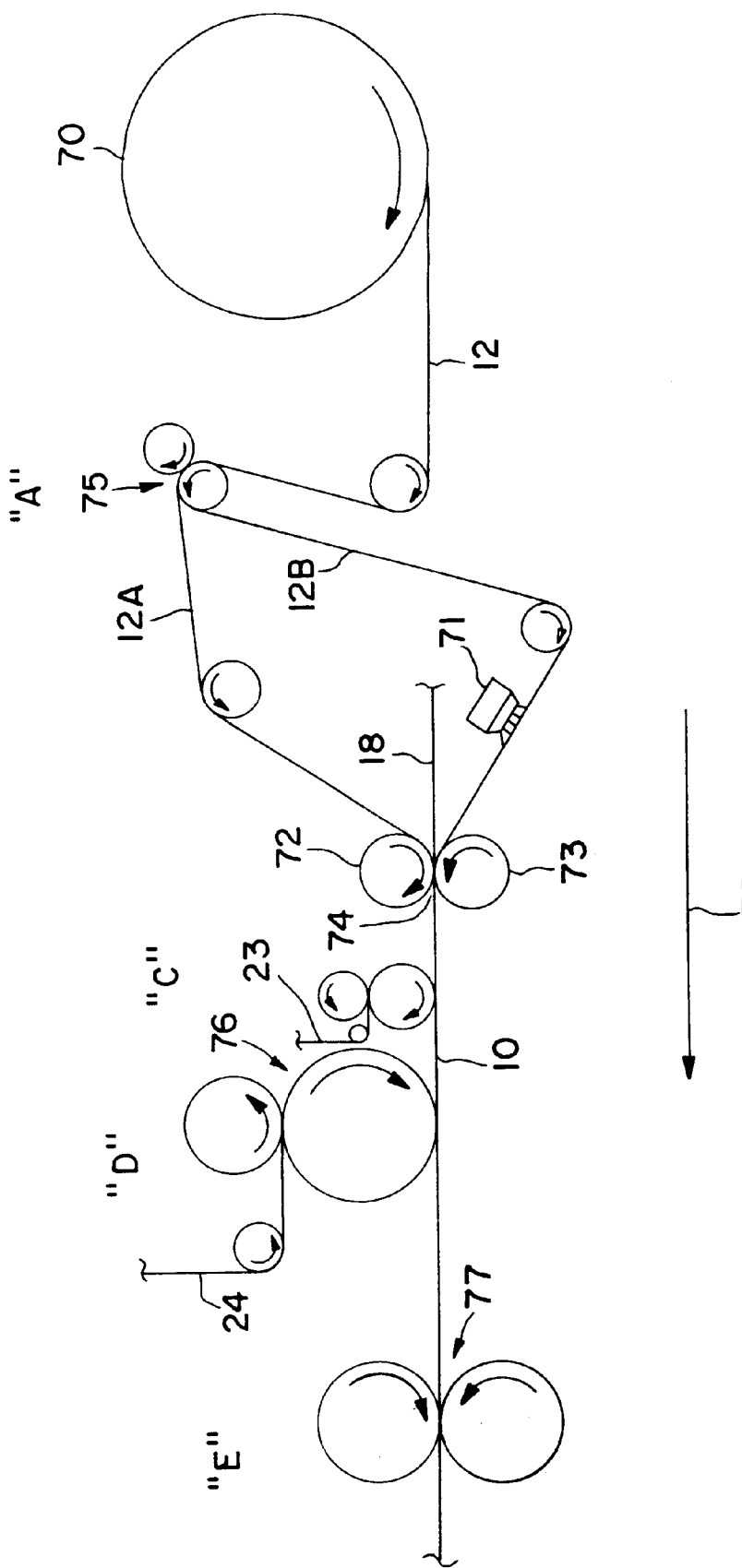
FIG. IC

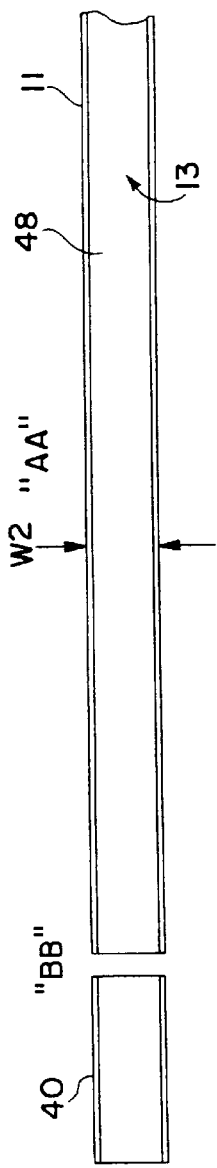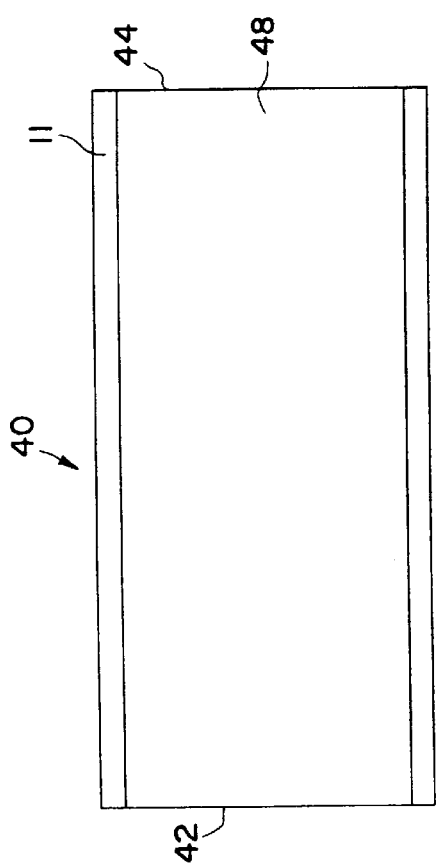
FIG. 2A
FIG. 2B

METHOD OF FABRICATING A MULTIPLE COMPONENT WEB

BACKGROUND

This invention relates to manufacture of, e.g. absorbent, personal care articles, especially to methods and apparatus for assembly of multiple component extensible webs, and personal care articles manufactured from such webs. More specifically, this invention relates to methods and apparatus for assembly of webs, preferably extensible webs, and personal care articles manufactured therefrom wherein the methods and apparatus of the invention diminish inefficient attributes of methods associated with conventional processes for manufacturing personal care articles. While embodiments of the present invention are described herein in terms of personal care articles such as pull-on pants or adult incontinence briefs, the invention includes, and is equally applicable to, infant diapers, training pants, and like personal care articles.

In conventional methods for fabricating personal care absorbent articles, it is known to build workplaces on a uniform, continuous web or webs as the web or webs advance through a series of work stations on a manufacturing line, wherein each work station effects a modification to a web or workpiece element, such as cuts or additions of absorbent article components to such web, webs, or workpiece element. Individual workplaces are then severed from the uniform continuous web or webs to form individual absorbent personal care articles or article blanks. In such conventional methods for fabricating personal care articles, ancillary components, such as fastener tabs and fastening areas or landing zones, are affixed to such articles or article blanks either at the work stations of such manufacturing line or at a subsequent stage in the manufacturing process after separation of such articles or article blanks from the web or webs.

A need exists for improved methods for production of personal care absorbent articles wherein the methods are effective to reduce material waste and to improve time efficiency of the manufacturing process as well as to reduce financial waste inevitably associated with time inefficiency of such manufacturing process. A need exists for improved methods for production of personal care absorbent articles wherein the methods are effective to attenuate material waste and time inefficiency associated with conventional manufacturing processes as well as to reduce the financial burden associated with such inefficiencies and waste.

Thus, it is an object of the invention to provide improved methods for production of personal care absorbent articles which implement a more "manufacture-friendly" extensible web as a base structure from which to assemble personal care absorbent articles, enabling a manufacturer to assemble such articles while employing relatively fewer work stations on the manufacturing line, compared to conventional methods, thus reducing production time.

It is another object of the invention to provide improved manufacturing methods which include fabricating a web of indefinite length by adding alternating workpieces and intervening elements to the web segment so as to develop a self-supporting web of indefinite length, wherein support of such self-supporting web along the indefinite length of such web is primarily defined by the alternating workpieces and intervening elements making up the web.

It is yet another object of the invention to provide improved manufacturing methods including defining, in the workpieces, mechanical fasteners effective to engage the intervening elements.

It is a further object of the invention to provide improved manufacturing methods wherein the releasable attachment of the workpieces to the intervening elements comprises the only attachment between the workpieces and the intervening elements.

It is a still further object of the invention to provide improved manufacturing methods which reduce the relative quantity of raw material which is wasted in the manufacturing of personal care-type articles.

SUMMARY

In a first family of embodiments, the invention comprehends a method of fabricating a web suitable for use in making a personal care absorbent article. The method comprises fabricating a resiliently extensible web by bringing together and securing to each other web substrate elements and resiliently stretchable elastic elements in stretched condition. The securement between the elastic elements and the web substrate elements is defined by alternating zones of securement and non-securement of the elastic elements to at least one of the web substrate elements along a length of the web substrate. The method also includes deactivating elastic elements in the non-securement zones thereby to attenuate resilient retraction of the web in such non-securement zones in response to activity of the elastics, and correspondingly, to distinguish the securement zones as relatively more resiliently stretchable and the non-securement zones as relatively less resiliently stretchable. The method further includes applying, to the relatively non-stretchable non-securement zones, patches of mechanical fastener material extending generally between respective adjacent ones of the relatively more resiliently stretchable securement zones.

In preferred embodiments, the invention comprises fabricating a workpiece suitable for use in a personal care article including defining a first end of such workpiece in the web by defining a free end of the web through a respective patch of the hook fastener material, and separating the workpiece from the web through a second respective patch of the hook fastener material such that hook fastener patch material is defined at opposing end portions of the respective workpiece.

In such preferred embodiments, the invention can comprise fabricating an extensible web from respective ones of first and second workpieces, wherein such web is suitable for use as a substrate in making a personal care article. The method comprises arranging workpieces in generally end-to-end relationship with intervening elements, and releasably attaching the hook material on the workpieces to hook receptive areas on the intervening elements, thus to releasably attach the workpieces to the intervening elements in fabricating a length of the extensible web.

The releasable attachment of the workpieces to the intervening elements comprises the primary structural attachment, and preferably the only attachment, between the workplaces and the intervening elements.

The method can comprise developing an alternating arrangement of the workpieces and the intervening elements such that each such workplace is between two such intervening elements and each such intervening element is between two such workpieces.

In some embodiments, the method comprises arranging workpieces in generally end-to-end relationship with intervening elements, respective ones of the intervening elements having lengths and widths defining respective surface areas, the hook receptive areas of such respective intervening elements generally corresponding to such surface areas. Such method includes releasably attaching the hook material on the workpieces to the intervening elements at the hook receptive areas, thus to releasably attach the workpieces and the intervening elements to each other in fabricating a length of the extensible web.

Methods of the invention typically include deactivating elastic elements in the non-securement zones preferably by cutting such elastic elements or by applying ultrasonic energy to such elastic elements optionally through an intervening layer.

In a second family of embodiments, the invention comprehends a method comprising fabricating a base web comprising multiple workpieces, applying patches of mechanical fastener material to such base web, and defining a first end of such workpiece by defining a free end of the base web through a respective patch of the fastener material, and separating the workpiece from the base web through a second respective patch of the fastener material such that a patch of fastener material is defined at both opposing end portions of the respective workpiece.

In preferred embodiments, the method includes arranging workpieces in generally end-to-end relationship with intervening elements, and releasably attaching the fastener material on the workpieces to fastener receptive areas on the intervening elements, thus to releasably attach the workpieces to the intervening elements in fabricating a length of composite web.

In some embodiments, the fastener material comprises a mechanical hook material.

In preferred embodiments, the intervening elements comprise a material which demonstrates fastener receptive properties, wherein the material of the intervening element is capable of forming engagement relationships with respective fastener materials.

In some embodiments, the method includes affixing the fastener receptive area, as a separate web element, to the intervening element, wherein the fastener receptive area has distinct physical edges.

In other embodiments, the fastener receptive area is integral with a major surface of the intervening element. The fastener receptive area is, thus, void of distinct physical edges.

In preferred embodiments, the base web comprises a neck-bonded laminate or a stretch-bonded laminate.

In a third family of embodiments, the invention comprehends a method of fabricating a self-supporting web of material from respective workpieces and intervening elements, wherein such self-supporting web is suitable for use as a substrate in making a personal care article. The method comprises bringing together an intervening element having first and second ends, a first workpiece having third and fourth ends, and a second workpiece having fifth and sixth ends, with first, second, and third lengths of the respective first and second workpieces and the intervening element aligned with each other in a generally common surface, and with the second and third lengths of the first and second workpieces operating as extensions of the first length of the intervening element, on opposing ones of the first and second ends of the intervening element. The method also includes releasably attaching the first workpiece and the intervening element to each other at the respective first and fourth ends, using releasable fasteners, and releasably attaching the second workpiece and the intervening element to each other at the respective second and fifth ends, using releasable fasteners, such that the first, second, and third lengths, in combination, define a self-supporting web segment having a fourth length. The fourth length of the web segment so defined by the combination of the first, second, and third lengths is greater than any of the first, second, and third lengths, individually, of the respective first and second workpieces and the intervening element. Additional such alternating workpieces and intervening elements can be releasably attached to one or both of the third and sixth ends of the respective first and second workpieces using additional releasable fasteners, to thereby further extend the length of the self-supporting web, wherein the releasable fasteners employed in so assembling the self-supporting web can be released so as to release respective ones of the workpieces and intervening elements of the self-supporting web from each other.

In some embodiments, the second and third lengths of the first and second workpieces are defined at rest, wherein the first and second workpieces are resiliently extensible by at least 100 percent of the respective second and third lengths, the method including attaching the first and second workpieces to the intervening element while the respective first and second workpieces are stretched substantially to stop.

In other embodiments, the method includes attaching the first and second workpieces to the intervening element while the respective first and second workpieces are being subjected to a stretching tension stretching the lengths of the respective first and second workpieces at least 50 percent from the respective second and third lengths.

In yet other embodiments, the first and second workpieces demonstrate effectively no elasticity. In such embodiments, the method involves substantially no stretching of the first and second workpieces, and simply includes attaching the first and second workpieces to the intervening element.

In preferred embodiments, the first and second workpieces are attached to the intervening element by fasteners having attachment capability over a substantial portion of an area defining the intervening element.

The first and second workpieces are preferably attached to the intervening element by first and second attachments defining mechanical fasteners on one of the respective workpieces and/or the intervening element interacting with mechanical loops on the other of the respective workplace and/or the intervening element.

In some embodiments, the method includes fabricating a web of indefinite length by adding alternating workpieces and intervening elements to the web segment so as to develop a self-supporting web of indefinite length wherein support of such self-supporting web along the indefinite length of such web is defined by the alternating workpieces and intervening elements making up the web.

Some embodiments of the method include defining, in the workpieces, mechanical fasteners effective to engage the intervening elements.

In a fourth family of embodiments, the invention comprehends a self-supporting web of sheet material suitable for use in making a personal care article, the self-supporting web comprising a sequence of at least first and second workplaces and intervening elements, including opposing ends on the respective workpieces and intervening elements. The respective workpieces and intervening elements have unstressed lengths between the respective ends thereof, the unstressed lengths of the respective workpieces and intervening elements being aligned with each other in a generally common surface, and operating as extensions of each other, such that the unstressed lengths, in combination, define a length of the web. The workpieces and intervening elements, in combination, generally define self-supporting longitudinal strength of the web. The workpieces and intervening elements are releasably attached to each other, using releasable fasteners, wherein the releasable fasteners employed in so assembling the web can be released so as to release respective ones of the workpieces and intervening elements from the self-supporting web.

In some embodiments, ones of the workpieces can be resiliently extended at least 100 percent from the unstressed lengths of the respective workpieces.

Preferred embodiments include employing hook and loop fastening structure in effecting the releasable fastening of the workpieces and intervening elements.

In a fifth family of embodiments, the invention comprehends a method of fabricating personal care absorbent articles. The method includes advancing along a processing line a first web having a first length. The first web is suitable for use in making a personal care article, and comprises at least workpieces and intervening elements releasably attached to each other using releasable fasteners to thereby define such first web and self-supporting longitudinal strength of such web, whereby such workpieces and intervening elements generally define the structure and the structural integrity of the first web. The method also includes concurrently advancing a second web having a second length along the processing line and generally parallel to the first web, and defining a space between the first and second webs, the second web being suitable for use in making such personal care article. The method further includes applying and attaching absorbent crotch portion elements to the first and second webs at spaced intervals along the lengths of the respective webs, and bridging the space between the first and second webs, thereby to form a composite web comprising the first and second webs and the respective crotch portions, wherein a given respective crotch portion element has a front segment attached to the first web and a rear segment attached to the second web. Additionally, the method includes bringing the first and second webs of the composite web into facing relationship with each other, including bringing the respective front and rear segments of the respective crotch portion elements generally into facing relationship with each other. The method also includes forming side seam bonds joining the first and second webs to each other at spaced locations along the length of the composite web, thereby to form a composite web sausage having an indefinite length. The method further includes separating discrete lengths of the composite web sausage from the indefinite-length composite web sausage at or proximate respective ones of the side seam bonds, thereby to define respective personal care articles.

In a sixth family of embodiments, the invention comprehends a personal care article comprising a front portion, a rear portion, and a crotch portion extending between the front portion and the rear portion. The front and rear portions each comprise opposing first and second side sections and a central section between the respective side sections, the rear portion and the front portion being attached to each other at respective side sections of the front and rear portions by side seams. The front portion comprises first and second workpieces corresponding to the side sections of the front portion, and an intervening element corresponding to the front central section, the first and second workpieces being releasably attached to the intervening element by releasable fasteners. The releasable fasteners, prior to use by a user, comprise the only attachment attaching the first and second workpieces to the front central section.

In preferred embodiments, the releasable fasteners comprise mechanical fasteners, received in hook receptive material defined at the intervening element.

In some embodiments, the first and second workpieces are attached to the intervening element by fasteners having attachment capability over a substantial portion of an area defining the intervening element.

In some embodiments, the first and second workpieces are attached to the intervening element by first and second attachments defining mechanical fasteners on one of the respective workpieces and/or the intervening element interacting with mechanical loops on the other of the respective workpieces and/or the intervening element.

BRIEF DESCRIPTION OF THE DRAWINGS

FIG. 1A shows a representative top view of a method of manufacturing resiliently extensible web components of the invention.

FIG. 1B shows a top view of a resiliently extensible web component of the invention.

FIG. 1C shows a representative side elevation view of a manufacturing line of the invention processing resiliently extensible web components of the invention.

FIG. 2A shows a representative top view of a process of manufacturing intervening elements of the invention.

FIG. 2B shows a top view of an intervening element of the invention.

Figure 3:
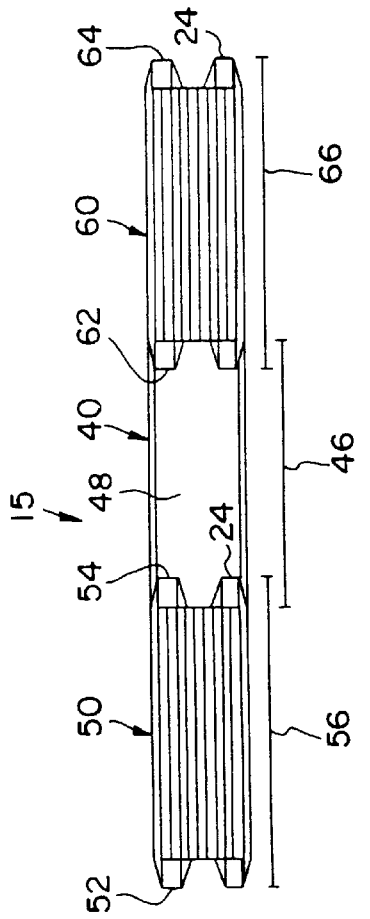
FIG. 3 shows a representative top view of an extensible web of the invention.
Figure 3:
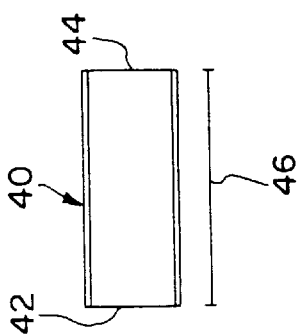
Figure 3:
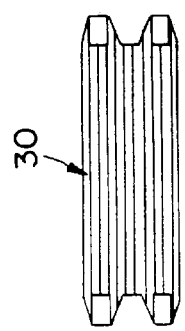

The invention is not limited in its application to the details of construction or the arrangement of the components set forth in the following description or illustrated in the drawings. The invention is capable of other embodiments or of being practiced or carried out in other various ways. Also, it is to be understood that the terminology and phraseology employed herein is for purpose of description and illustration and should not be regarded as limiting. Like reference numerals are used to indicate like components.

DESCRIPTION OF THE ILLUSTRATED EMBODIMENTS

Referring to FIG. 1A, the invention comprehends apparatus and methods for fabricating a web suitable for use in making personal care absorbent articles. Respective segments of the exemplary illustrated manufacturing process of the invention are indicated by letters "A–F". Process segments "A, C, D, E" of FIG. 1C correspond with respective process segments "A, C, D, E" of the process shown in FIG. 1A.

Referring to FIG. 1C, at the segment of the method illustrated at "A", web substrate 12 is fed into the process by web unwind 70. Web substrate 12 is slit by e.g. a web slitter 75 and separated to form two separate and distinct webs 12A, 12B. Webs 12A and 12B are routed along separate distinct manufacturing pathways wherein adhesive is intermittently applied to web 12B using adhesive applicator 71 thereby to create alternating longitudinally-spaced coated web segments and uncoated web segments. In some embodiments, the two webs e.g. 12A, 12B have separate and distinct origins on the manufacturing line.

Webs 12A and 12B come together in face-to-face relationship as the respective separate manufacturing pathways of webs 12A, 12B approach one another to enable webs 12A, 12B to once again follow a common path of manufacture. As webs 12A, 12B approach one another, elastic elements 18 are fed between webs 12A, 12B, in stretched to stop condition, at a nip 74 formed by first pressure roll 72 and second pressure roll 73, such that elastic elements 18 are substantially aligned with machine direction 78. The force exerted in the nip created by first and second pressure rolls 72, 73 urges webs 12A, 12B together and, due to the adhesive applied to web 12B, effects an adherent joinder of webs 12A, 12B encompassing elastic elements 18 therein thus forming an stretchable extensible web 10 as shown at segment "A" of FIG. 1A having alternating bonded and unbonded longitudinally-extending web segments. Webs 12A, 12B, and the intervening elastic strands are bonded to each other at the bonded web segments, and are not bonded to each other at the unbonded web segments. The bonded web segments generally correspond to the adhesively-coated web segments, and the unbonded web segments generally correspond to the adhesively-uncoated web segments.

While webs 12A, 12B are shown as being affixed to one another using adhesive. Other methods of joining two or more webs to each other with elastic elements therebetween, including ultrasonic bonding and thermal bonding, will be obvious to those of ordinary skill in the art.

The inclusion of stretched elastic elements 18 in the fabrication of web 10 results in retraction of the web as the elastic elements contract to a relaxed state when released from the manufacturing process, wherein the elastic elements reflect a lack of stress in machine direction 78 of the resulting fabricated web. Methods of the invention can be achieved, albeit with somewhat less efficiency, when web 10 proceeds through subsequent segments of the process having elastic elements 18 in extensible web 10 partially stretched or contracted to a substantially relaxed state. Thus, throughout the web fabricating methods and thus the manufacturing process of the invention, elastic elements 18 of extensible web 10 are preferably stretched to stop to enable precision in implementation of method effects, wherein the respective distance between respective adjacent method activities, e.g. formation of non-securement zone at segment "B" of FIG. 1A, remains substantially constant, from web portion to web portion.

As used herein, "stretching to stop" refers to stretching a workpiece or other element to the full extent consistent with integrity of the workpiece or element being stretched, without damage to the workplace or element, and without substantial irreversible stretching of resiliently stretchable such workplace or element.

While, for clarity, FIG. 1A shows elastic elements 18 only at portions of the manufacturing process illustrated in FIG. 1A, it should be understood that such elastic strands are typically spaced along the full widths, and extend along the full lengths, of web 10, and that correspondingly, such properties generally carry through to all of process segments "A–F" indicated in FIG. 1A.

In some embodiments, a substantially uniform distribution of adhesive coating exists throughout the effective entirety of the web between webs 12A, 12B. In such embodiments, the activity or inactivity of the elastics does not necessarily depend upon whether adhesive has been applied to the respective area of the web, but whether the elastics have been inactivated via a severing process as discussed above.

Segment "B" of the process illustrates that elastic elements 18 are preferably severed at the uncoated segments of the web, namely those web segments lacking adhesive. Elastic elements 18 disposed on and/or in extensible web 10 can thus be deactivated by such severing such using e.g. a rotary die cutter, by melt-breaking such elastic using e.g. a heated or ultrasonic function roll, or by any other means known to those skilled in the art for deactivating elastics. Typically, such deactivation breaks the respective elastic strand at an uncoated segment of the web whereby the elastic strand retracts to the edge of the adjacent coated segment of the web. Such severing thus deactivates the elastic tension at those adjoining portions of the respective elastic elements which are not secured to the respective e.g. web 10 by sufficient securement means e.g. adhesive to counteract such retractive forces. Thus, upon severance, the elastic elements, to the extent stretched, and not adhered to the web, retract into a generally unstressed condition adjacent the adjoining coated/bonded web segment, thereby forming respective non-securement zones 22. The area over which the elastic elements so retract, non-securement zones 22, suggested by the light sporadic lines at segment "B", are thenceforth inactive as far as resilient stretching imparted by the elastic elements. Conversely, securement areas 20 define the areas over which elastic elements 18 maintain resilient stretching characteristics relative to non-securement zones 22, the conservation of resilience of such securement areas being due to adherently pairing respective loci of elastic elements 18 to respective loci of webs 12A, 12B (FIG. 1C) using e.g. adhesive, such elastics of such securement zones 20 being illustrated by the aligned uniform lines at segment "B". Securement zones 20 generally correspond to the coated segments of the web 12B. Correspondingly, non-securement zones 22 generally correspond to uncoated segments of web 12B.

In other embodiments, web 10 does not include defined strands of elastic elements, per se, but comprises web material which demonstrate resiliently stretchable properties such as stretch-bonded laminate material, neck-bonded laminate material, and/or composite elastomeric material. In yet other functional, yet less preferable embodiments, web 10 can comprise little or no elastic wherein such web exhibits minimal, if any, elastomeric properties.

Regarding any of the aforementioned embodiments, some sub-sets of such embodiments having elastic strands, elements, or properties do not include deactivating elastic properties in any portion of web 10. In such embodiments, web 10 is preferably stretched to stop throughout the manufacturing process to enable precision in placement and/or affixation of subsequent web elements.

At segment "C" of the manufacturing process illustrated in FIG. 1A and FIG. 1C, reinforcement patches 23 are disposed onto non-securement zones 22 of extensible web 10. Such reinforcement patches are affixed to the non-securement zone using a known means of affixing first and second web elements to one another, preferably adhesive and/or ultrasonic bonding.

Reinforcement patch 23 can comprise a variety of woven and nonwoven fabrics. For example, reinforcement patch 23 can be a non-woven web of polymeric material selected from the group consisting of polyolefins including polyethylenes and polypropylenes, polyesters, and polyamides, and mixtures, copolymers, and blends of such polymeric fibers. Reinforcement patch 23 can also comprise a carded and/or bonded web composed of natural and/or synthetic fibers. Reinforcement patch 23 typically comprises a fibrous web defining a multiplicity of small e.g. microporous openings randomly spaced between the fibers and according to location and orientation of the fibers, extending from a major surface of the web into the interior of the web. Such small openings typically extend through the entirety of the thickness of the web.

Reinforcement patch 23 can be fabricated using structural components selected from the group consisting of porous foams, reticulated foams, apertured polymeric films, polymeric fibers, and natural fibers, and such patch can comprise a multiplicity of components or layers which correspond to any of the materials disclosed herein, as well as others known in the art.

At segment "D" of the manufacturing process illustrated in FIGS. 1A, 1C, fastener material 24 is bonded to at least a portion of reinforcement patch 23 of extensible web 10 using ultrasonic energy applied by e.g. ultrasonic bonding apparatus. As an alternative to ultrasonic energy, such bonding can be implemented using e.g. thermal energy, adhesives, or a combination of adhesives with ultrasonic energy or thermal energy.

Some embodiments comprise fastener material which effectively spans substantially the entire width "W1" of extensible web 10 wherein the width of the web defines the distance between most remote portions of web 10 perpendicular to machine direction 78. In such embodiments, fastener material 24 is preferably, but not necessarily, cut and trimmed in a subsequent step(s) of the process.

Referring back to segment "C" of the process, reinforcement patch 23 is preferably affixed to non-securement zone 22 to provide structural integrity to web 10. However, some embodiments do not include the application of a reinforcement patch to the web. In such embodiments, fastener material is bonded directly to web 10 using one or more of ultrasonic energy, thermal energy, adhesives, or any other means of affixing a fastener material to a web known to those of ordinary skill in the art.

Fastener material 24 defines an attachment structure(s) which, e.g. in combination with the fastener receptive area, can be repeatedly fastened, released, adjusted and re-fastened. Acceptable embodiments of fastener material can include any material capable of forming cooperative engagement relationships with the respective material used for the fastener receptive area(s). For example and without limitation, such acceptable fastener materials are adhesives, cohesives, tapes, mechanical fasteners such as buttons and corresponding buttonholes, snaps and the like, as well as other fasteners which can be repeatedly fastened and released known to those skilled in the art. Mechanical hook and loop fasteners are preferred because of their associated versatility and cost effectiveness.

Figure 4:
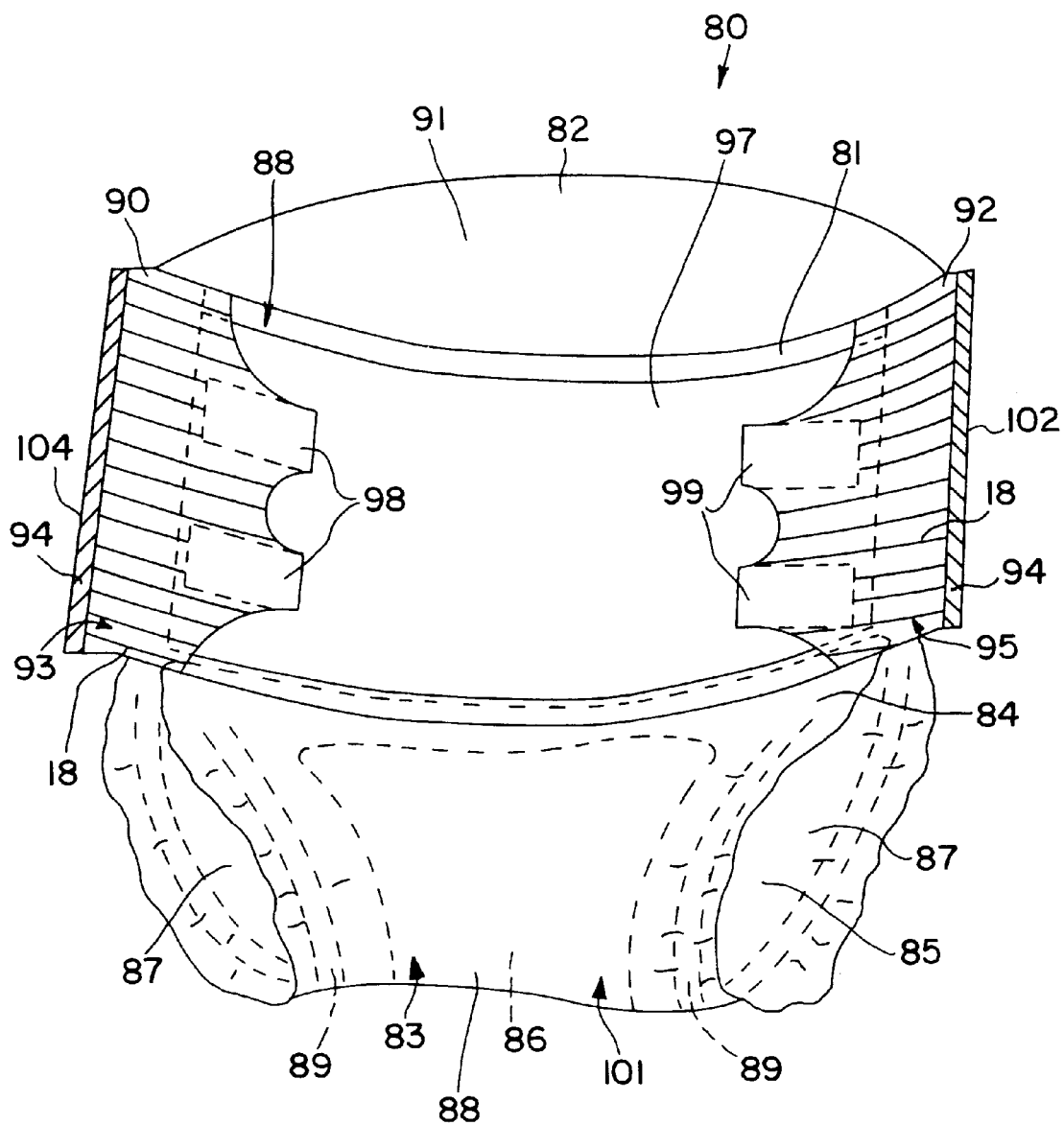
FIG. 4 shows a pictorial view of a representative personal care article of the invention.

Segment "E" of the manufacturing process of FIGS. 1A, 1C shows optional die-cuts 25A, 25B, 25C being effected preferably entirely through fastener material 24, through reinforcement patch 23, and through underlying web 10 using e.g. die/cut-out apparatus 77 to preferably shape the area of the web comprising fastener material 24, thereby e.g. improving conduciveness of such areas, upon further processing into fasteners 98, 99, to wearer manipulation of a resultant personal care absorbent article 80 of FIG. 4.

Some embodiments have fastener material, and optionally reinforcement patches, that does not require subsequent trimming. In such embodiments, segment "E" is omitted from the process.

At segment "F" of the manufacturing process illustrated in FIG. 1A, individual resilient web elements or web articles are preferably severed from extensible web 10 thus to define individual separate and discrete webs 30 suitable for use in making personal care absorbent articles. Such severing can be effected by a cutting of the assembled web in a cross-machine direction at desired spaced web locations using e.g. a knife and anvil cut-off. Such cut is made in the cross-machine direction through respective reinforcement patches 23 and fastener material 24 bonded to such reinforcement patches, as well as through webs 12A, 12B, and any elastic elements 18 which may not have fully retracted when cut at process segment "B".

Rather than severing or separating individual separate and discrete resilient webs 30 at fastener material 24 as illustrated, the respective cuts can be effected, instead, at an in-line production station in a subsequent stage of an absorbent article manufacturing process wherein web 10 is processed and incorporated into absorbent articles.

In alternative methods, the respective cuts can be effected, instead, as lines of weakness such as, e.g. perforations, an array of cuts, or the like, with complete severance at every "n" workpieces. Such process results in strips of respective separate and discrete resilient webs 30, each strip containing "n" resilient webs 30. The strip can then be rolled up for processing into personal care absorbent articles, or packaging and shipping of such rolled up strip to a manufacturer of personal care absorbent articles.

FIG. 1B illustrates a resilient web 30 fabricated using methods of the invention illustrated in FIGS. 1A, 1C, and cut off as a single web workpiece. Resilient web 30 comprises a first end 14 and a second end 16. A first patch 26 of fastener material is disposed at first end 14 of resilient web 30, and similarly, a second patch 28 of fastener material is disposed at second end 16 of resilient web 30. First and second patches 26, 28 of fastener material are disposed on and bonded to respective portions of reinforcement patches 23 which are, in turn, affixed to one of webs 12A, 12B.

In alternative embodiments, resilient web 30 does not include elastic elements, per se, but comprises web material which demonstrate elastomeric properties such as stretch-bonded laminate material, neck-bonded laminate material, and/or composite elastomeric material such as those described in U.S. Pat. No. 4,863,779 herein incorporated by reference in its entirety. Other embodiments can comprise elastic at least in and/or on portions of resilient web 30. Other less preferable embodiments comprise little or no active elastic in and/or on web 30, thus resulting in a web which demonstrates substantially no elastomeric properties.

Referring to FIGS. 2A, 2B, the invention comprehends apparatus and methods for fabricating an intervening element 40 suitable for cooperative use as an attachment surface for affixing ones of resilient webs 30 thereto. As with the processes of FIGS. 1A, 1C, respective segments of the respective exemplary illustrated manufacturing process of the invention are alphabetically designated in FIG. 2A, indicating such segments using letters "AA–BB".

Referring to FIG. 2A at the segment of the method illustrated at "AA", landing zone material 48 is superimposed on substrate web 11 in a surface-to-surface relationship and bonded or otherwise affixed to such web to form receiver web 13. In some embodiments, the landing zone material has a width substantially equal to the width "W2" of web 11, each width defining the cross-machine direction distance between most remote portions of the respective material or web. In other embodiments, the landing zone material has a width less than the width of web 11. Whereas landing zone material 48 is preferably affixed to web 11 while each of web 11 and landing zone material 48 is in the form of a continuous web, some embodiments include one or both of landing zone material 48 and web 11 being applied as segments or fragments to the other of such material or web.

As used herein "affixing" means joining webs and/or web components using adhesive, heat, ultrasonic bonding, and/or other known means of bringing webs together to form a combined unit. "Affixing" shall encompass intermittently or entirely effecting such bringing together across a surface of one or more of the desired webs and/or components, point and/or partial areal applications of such uniting means, and any other means of joining landing zone material 48 to web 11 such that resultant receiver web 13 fares as a unitary composite web.

At segment "BB" of the manufacturing process illustrated in FIG. 2A, individual intervening elements 40 are preferably severed from receiver web 13 thus to define individual separate and distinct intervening elements 40 suitable for use in making personal care absorbent articles. Such severing can be effected by a cutting of the assembled web in a cross-machine direction at desired spaced web locations using e.g. a knife and anvil cut-off. Such cut is made in the cross-machine direction preferably passing through both web 11 and landing zone material 48.

As with the methods of FIG. 1A, rather than completely severing or separating individual separate and discrete intervening elements 40 from receiver web 13 as illustrated in FIG. 2A, the respective cuts can be effected, instead, at an in-line production station in a subsequent stage of an absorbent article manufacturing process wherein receiver web 13 is processed and incorporated into absorbent articles.

Alternatively, the respective cuts in the receiver web can be effected as lines of weakness such as, e.g. perforations, an array of cuts, or the like, with complete severance at every "n" workpieces. Such process results in strips of respective separate and discrete intervening elements 40, each strip containing "n" intervening elements 40. The strip can then be rolled up for processing into personal care absorbent articles, or packaging and shipping of such rolled up strip to manufacturers of personal care absorbent articles.

FIG. 2B illustrates an intervening element 40 fabricated using methods of the invention, such intervening element having a first end 42 and a second end 44, and comprising at least web 11 and landing zone material 48.

The patch of landing zone material 48 typically encompassing substantially the entireties of the lengths and the widths of web 11. While the patch of landing zone material 48 is illustrated as being a one-component, generally rectangular-shaped piece of landing zone material, the landing zone material, comprising a fastener receptive area, can be defined by a variety of shapes and sizes, and any desired number of separate components.

Landing zone material 48 can comprise material which preferably has e.g. loop properties or hook material properties. In the alternative, any material which can form a cooperative relationship with desired fastener materials, such as those suggested in the discussion of segment "D" of the process, to provide repeatable fastening and releasing properties is suitable for use as, or in place of, landing zone material 48 as long as such material's engagable compliment is used as the fastener material.

In some embodiments, web 11 comprises a material which inherently demonstrates landing zone properties capable of forming engagement relationships with respective fastener materials defined in step "D" of the process. In such embodiments, the step of the manufacturing process, which includes applying a patch of landing zone material 48 to web 11, is not included in the process since at least a portion, and up to the entirety, of the major surface of web 11 already includes fastening area properties.

Therefore, a landing zone may or may not have distinct physical edges, depending on whether the fastening properties desired to be performed thereby (i) are provided by distinct separate e.g. web element(s) or (ii) are integral with a surface of front portion web 26.

FIG. 3 illustrates a resilient web 30 of the invention, e.g. of FIGS. 1A, 1B, and an intervening element 40 of the invention, e.g. of FIGS. 2A, 2B. FIG. 3 also illustrates how resilient web 30 and element 40 can be engaged to form a self-supporting composite web 15 having a first resilient web workpiece 50, a second resilient web workpiece 60, wherein each of first and second resilient web workpieces 50, 60 comprises a resilient web 30, and an intervening element 40 between such first and second resilient web workpieces 50, 60. Intervening element 40 has a first end 42, a second end 44, and a third length 46. Similarly, first resilient web workpiece 50 has a third end 52, a fourth end 54, and a first length 56; and second resilient web workpiece 60 has a fifth end 62, a sixth end 64, and a second length 66.

In FIG. 3, fastener material 24 is affixed to a major surface at least near each end of each respective resilient web workpiece e.g. 50, 60, so as to allow such fastener material of such resilient web workpiece to overlie and thus create a cooperative engagement relationship with landing zone material 48 of the respective intervening element e.g. 40, wherein a portion of the respective length e.g. 56, 66 of such resilient web workpiece e.g. 50, 60 overlies a portion of the length e.g. 46 of the respective intervening element.

Fastener material 24 as illustrated herein defines attachment structures which, e.g. in cooperation with landing zone material 48, or the like, can be repeatedly fastened, released, adjusted and re-fastened to the landing zone material. Acceptable embodiments of fastener material 24 can include any material capable of forming cooperative engagement relationships with the respective material used as or on the landing zone area defined by landing zone material 48. For example and without limitation, such acceptable fastener materials are adhesives, cohesives, mechanical fasteners such as buttons and corresponding buttonholes, snaps and the like, as well as other fastener materials which can be repeatedly fastened and released, known to those skilled in the art. Mechanical hook and loop fasteners are preferred because of their associated durability and consumer acceptance. In some embodiments, hook material, and the like, commonly used in the art as fastener material, is employed in the landing zone area of element 40, and cooperating loop material, and the like, commonly used in the art as landing zone material, is employed in the fastener areas of workplaces 50, 60.

The landing area can be occupied and effected by material which preferably has e.g. loop properties or hook material properties. In the alternative, any material which can form a cooperative relationship with desired fastener materials, such as those suggested in the discussion above of the process, to provide repeatable fastening and releasing properties is suitable for use as, or in place of, landing zone material 48.

A continuous composite web of indefinite length, or substantially any desired length, can be constructed by bringing together alternating ones of resilient webs 30 and intervening elements 40, generally as illustrated in FIG. 3. As seen in FIG. 3, fastener elements 24 on respective resilient webs 30 overlie end portions of adjoining intervening elements 40. By applying pressure urging the fasteners and intervening elements together, the fasteners become affixed to the intervening elements thus to join the resilient web to the respective intervening element. Such joining can be effected at respective overlying/overlapping portions of resilient webs and intervening elements at respective ends of a so-constructed length of composite web. For example, the composite web illustrated in FIG. 3 contains three components, namely, first and second resilient webs 50, 60, and intervening element 40. The composite web of FIG. 3 can be extended to any desired length by adding additional components. For example, a second intervening element (not shown) can be added at end 64 of workpiece 60 in a relationship reflecting that shown by the intervening element 40 which is shown, thus to make a 4-component composite web. Similarly, a third resilient web 30 can be added on the distal end of the second intervening element thus to make a 5-component composite web.

Each such component is joined in the web by urging the respective fasteners and receptor e.g. loop material toward each other at the overlapped end areas. The joinder so formed e.g. by hook and loop fastener system, is effective to provide primary structure and strength to the web between the respective web components. As contemplated herein, such joinder at the fasteners provides the sole structure and strength of the web between the respective web components. Such web is thus well represented by a repeated iteration of resilient web—intervening element—resilient web—intervening element, in as many repeated iterations as desired.

Such composite web can be formed independently in an off-line process and e.g. wound up in roll form for future use. In the alternative, such composite web can be formed on line, as one feed stream into a manufacturing line which is fabricating personal care, e.g. absorbent article, an assembly portion of such manufacturing process being illustrated in FIG. 5.

Figure 5:
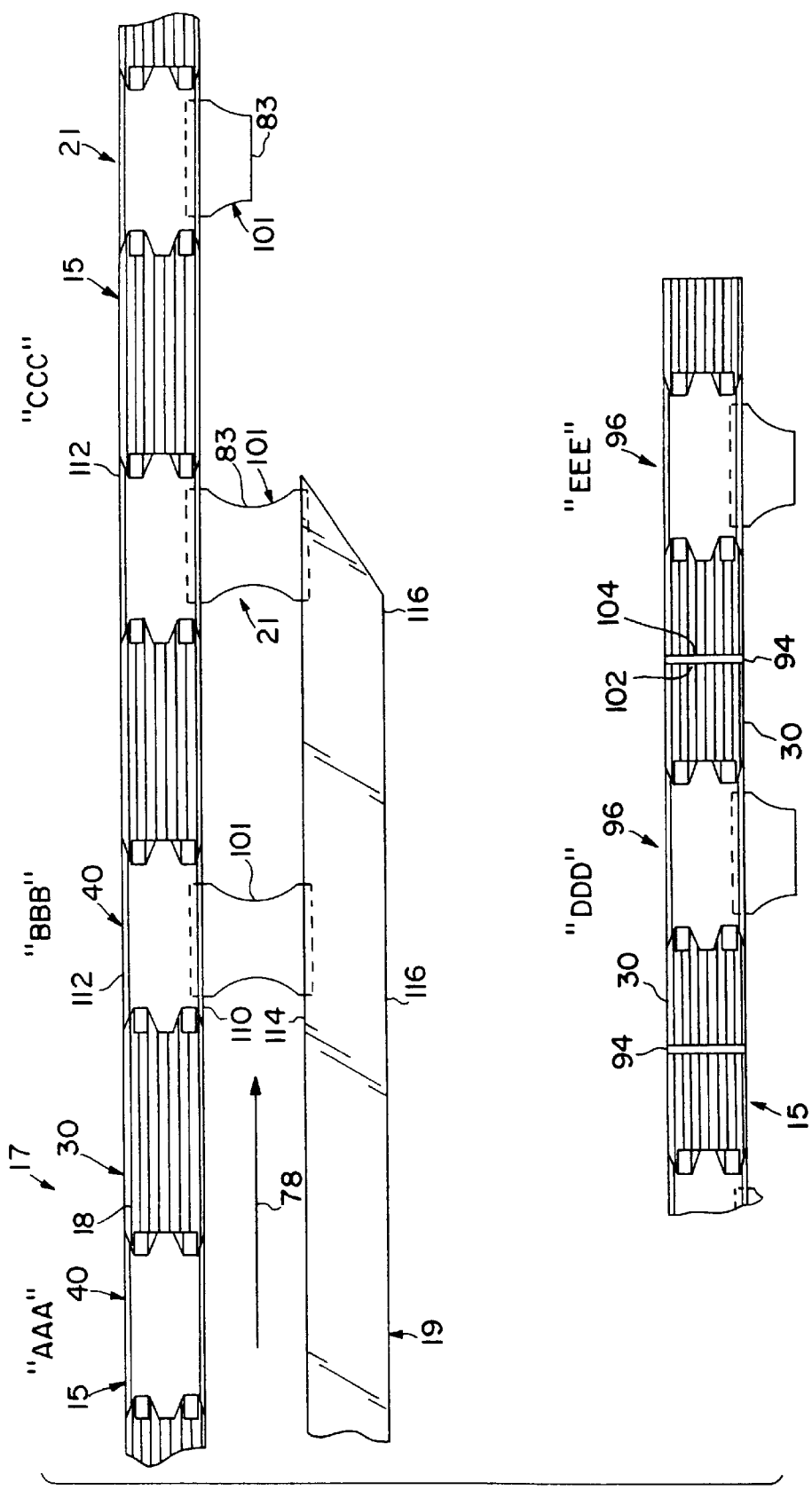
FIG. 5 shows a top view of a representative assembly method for fabricating personal care articles of the invention.

Referring to FIG. 5, the invention comprehends methods for assembling personal care absorbent articles. Respective segments of the exemplary illustrated manufacturing process of the invention are indicated by letters "AAA–EEE".

At the segment of the method illustrated at "AAA", a stream of workpieces 17, representative of composite web 15 of FIG. 3, travels along a manufacturing path in the machine direction indicated by directional arrow 78. In the embodiment illustrated in FIG. 5, stream of workpieces 17 is representative of the self-supporting composite web 15 and rear web 19, as well as any other personal care article components employed or affixed, both directly and indirectly, to such webs.

While only resilient webs 30 of self-supporting web 15 are illustrated comprising elastic elements 18 in FIG. 5, some embodiments comprise elastic elements in and/or on at least portions, up to substantially the entirety, of rear web 19 as well.

At segment "BBB" of the manufacturing process, crotch element 101 is attached to intervening element 40 of self-supporting web 15 at least at or near inner edge 110 of intervening element 40, and to rear web 19 at least at or near inner edge 114 of rear web 19. In the illustrated embodiment, crotch element 101 is attached to surfaces of intervening element 40 and rear web 19 which surfaces are directed away from the viewer. Accordingly, crotch element 101 is shown in dashed outline at the respective intervening elements 40 and webs 19. FIG. 4 shows crotch element 101 in solid outline. The attachment of crotch portion 101 to web 15, 19 operates as a unifying bridge joining webs 15, 19 to each other as a web sausage 21.

Crotch element 101 generally comprises a substrate web, supporting an absorbent core 86, and leg elastic 89 (FIG. 4), although such components can be added to crotch element 101 during other portions of the manufacturing process. Crotch element 101 is preferably attached to intervening element 40 and rear web 19 via adhesives, although other attachment means known to those skilled in the art are contemplated, for example ultrasonic bonding.

At segment "CCC" of the manufacturing process, web sausage 21 is folded at centrally-disposed crotch portion 83 of crotch element 101 such that self-supporting web 15 and rear web 19 are disposed in an overlying and facing relationship with one another wherein respective outer edges 112, 116 of respective webs 15, 19 preferably, but not necessarily, are substantially overlying one another. Such folding of web sausage 21 can be effected using a folding mechanism such as, but not limited to, a helical folder or a folding bar.

As used herein, "web sausage" includes single and multiple webs, or multiple web elements and components thereof, used as basis or other substrate upon which to build personal care absorbent article workpieces. Where multiple webs are used, a second such multiple web can overlie a first such web, or, as illustrated in FIG. 5, first and second webs can be advanced in a side-by-side arrangement, spaced from each other.

At segment "DDD" of the manufacturing process of FIG. 5, side seam bonds 94 are formed adhering portions of resilient web 30 of self-supporting composite web 15 to rear web 19 between respective adjacent individual workpiece precursors 96. Bonds 94 are preferably formed using ultrasonic energy applied by e.g. ultrasonic bonding apparatus. As an alternative to ultrasonic energy, side seam bonds 94 can be implemented using e.g. thermal energy, adhesives, or a combination of adhesives with ultrasonic energy or thermal energy.

At segment "EEE" of the manufacturing process, individual workpiece precursors 96 are preferably severed from the web sausage thus to define individual separate and distinct finished personal care article products. Such severing can be effected by a cutting in a cross-machine direction along each respective side seam 94 using e.g. a knife and anvil cut-off. Such cut is made between edges 102, 104 so as to define a bonded such side seam on each of the two articles so defined at each respective cut.

In alternative methods of manufacturing personal care articles comprising resilient webs of the invention, a segment of web 15 of FIG. 3 can be severed from such web 15, the segment of web 15 comprising intervening element 40, a portion of resilient web 50 including fourth end 54, and a portion of resilient web 60 including fifth end 62. Referring also to FIGS. 4 and 5, the segment of web 15 can subsequently be incorporated into a personal care article precursor/web sausage by bonding most remote areas of respective portions of resilient webs 50, 60 of the segment of web 15 to respective side sections 90, 92 using side seams bonds 94 at respective edges 102, 104 of the personal care article precursor/web sausage wherein resilient webs 50, 60 are bonded to the respective side sections using adhesive or ultrasonic bonding, although other affixation means known to those skilled in the art are contemplated. Intervening element 40 is thus joined to the respective personal care article precursor/web sausage of the invention by affixing such intervening element to crotch element 101 of such personal care article precursor/web sausage using e.g. adhesive as an affixation agent.

FIG. 4 illustrates a personal care absorbent article 80 of the invention including a front portion 81 having a central section 88, a first side section 90, and a second side section 92, a rear portion 82 and crotch portion 83. Additionally, personal care absorbent article 80 also comprises an absorbent core 86 mounted between bodyside liner 85 and outer cover 84. Landing zone 97, typically comprised in intervening element 40, is disposed at an outer surface e.g. of central section 88 of front portion 81 and cooperates with first fasteners 98 of a first lateral section 93, and second fasteners 99 of a second lateral section 95 in creating a cooperative engagement relationship. Such engagement relationship enables a user, in combination with elastic elements 18 of lateral sections 93, 95, to fasten, unfasten and re-fasten fasteners 98, 99 on landing zone 97 thereby to adjust waist sizing of the personal care absorbent article. During use, and optionally during packaging, each of the fasteners, e.g. second fastener 99, is releasably secured to landing zone 97. Lateral sections 93, 95 are typically derived from resilient webs 30 through e.g. workpieces 50, 60.

Leg elastics 89 are shown extending generally along the areas peripheral to opposing sides of absorbent core 86, following the contour of personal care absorbent article 80, through crotch portion 83 and ending at or near front portion 81 and rear portion 82. Leg elastics 89 function to gather the material at the side edges of crotch portion 83 along leg openings 87. Leg openings 87 are formed as apertures in the personal care absorbent article as front portion 81 is secured to rear portion 82 via side seam bonds 94 at edges 102, 104 thus to form a personal care article e.g. as illustrated in FIG. 4.

Various types of elastic materials are known for use in leg elastics 89. Leg elastics 89 typically provide overall retractive tensions of from about 10 grams to about 400 grams on a given leg opening at stretch-to-stop conditions. Preferably, leg elastics 89 provide tensions of about 50 grams to about 220 grams. More preferably, leg elastics 89 provide tensions of about 80 grams to about 200 grams.

The personal care absorbent article of FIG. 4 includes significant portions of self-supporting composite web 15 of FIG. 3. Referring to FIGS. 3, 4, landing zone 97 of central section 88 of front portion 81 of personal care absorbent article 80 comprises an intervening element 40 manufactured using the process described with respect to FIGS. 2A, 2B. First lateral section 93 and second lateral section 95 each comprise a significant portion of first and second resilient web workpieces e.g. 50, 60.

A variety of materials can be employed as components of web 11 (FIG. 2A) and/or web substrate 12 (FIG. 1A), in fabricating personal care articles of the invention. Various woven and nonwoven fabrics can be used for bodyside liner 85, as well as any or all of web 11, substrate web 12, and web 19. For example, bodyside liner 85 and/or one or more of web 11, substrate web 12, and web 19 can comprise one or more of e.g. a melt-blown, spunbonded, or other non-woven web of polymeric material selected from the group consisting of polyolefins including polyethylenes and polypropylenes, polyesters, and polyamides, and mixtures, copolymers, and blends of such polymeric fibers. Bodyside liner 85 and/or any one of web 11, substrate web 12, or web 19 may also comprise a carded and/or bonded web composed of natural and/or synthetic fibers. The bodyside liner and/or any one of web 11, substrate web 12, or web 19 can be composed of a substantially hydrophobic material wherein the hydrophobic material is treated with a surfactant or otherwise processed to impart a desired level of wetability and hydrophilicity.

Bodyside liner 85 and/or any one of web 11, substrate web 12, or web 19 can comprise nonwoven, spunbonded, polypropylene fabric fabricated with 2.8–3.2 denier fibers, formed into a web having a basis weight of e.g. about 22 grams per square meter and a density of e.g. about 0.06 grams per cubic centimeter. The fabric is preferably surface treated with e.g. about 0.3 weight percent of a surfactant. Bodyside liner 85 and/or any one of web 11, substrate web 12, or web 19 typically comprises a fibrous web defining a multiplicity of small e.g. microporous openings randomly spaced between the fibers and according to location and orientation of the fibers, extending from a major surface of the web into the interior of the web. Such small openings typically extend through the entirety of the thickness of the web.

Addressing structure, bodyside liner 85 and/or any one of web 11, substrate web 12, or web 19 can be fabricated using material selected from the group consisting of porous foams, reticulated foams, apertured polymeric films and laminates, polymeric fibers, and natural fibers. Bodyside liner 85 and/or any one of web 11, substrate web 12, or web 19 can comprise a multiplicity of components or layers which correspond to any of the materials disclosed herein, as well as to others known in the art.

It is generally preferred that outer cover 84 of crotch portion 83 and rear portion 82 of the personal care article be formed from a material which is substantially impermeable to liquids. A typical outer cover 84 for crotch portion 83 and rear portion 82 can be manufactured from a thin plastic film or other flexible liquid-impermeable material. For example, outer cover 84 can be formed from a film of polymeric material selected from the group consisting of polyolefins including polyethylenes and polypropylenes, polyesters, and polyamides, and mixtures, copolymers, and blends of such polymeric materials, having thicknesses, for example, of from about 0.012 millimeter to about 0.13 millimeter.

In embodiments where outer cover 84 of crotch portion 83 and rear portion 82 should have a more cloth-like feel, the outer cover can comprise a polyethylene film having a nonwoven web, such as a spunbonded web of polyolefin fibers, bonded to a surface thereof. For example, a polyethylene film having a thickness of about 0.015 millimeter can have thermally or otherwise bonded thereto a spunbonded web of polyolefin fibers having fiber thicknesses of from about 1.5 to about 2.5 denier per filament, which spunbonded web has a basis weight of e.g. about 24 grams per square meter.

Further, outer cover 84 of crotch portion 83 and rear portion 82 can be formed of a woven or nonwoven fibrous web which has been totally or partially constructed or treated to impart a desired level of liquid impermeability to selected regions which are e.g. adjacent or proximate absorbent core 86.

Still further, outer cover 84 of crotch portion 83 and rear portion 82 can optionally be composed of a micro-porous material which permits vapors to escape from absorbent core 86 and through outer cover 84 while preventing liquid exudates from passing through the outer cover.

One or both of outer cover 84 and bodyside liner 85 can comprise a fibrous web defining a multiplicity of randomly-spaced small openings extending from a major surface of the web into the interior of the web. Polymeric material such as the recited polyolefins including polyethylenes and polypropylenes, polyesters, and polyamides, and mixtures, copolymers, and blends of such polymeric materials can be used in either film form or in non-woven fiber form, for one or both of bodyside liner 85 and outer cover 84. As to bodyside liner 85, films are apertured films. As to outer cover 84, fibrous webs are impermeable to e.g. aqueous liquid.

Included in the definition of polymeric material above are all routine, common, normal additives known to those skilled in the art of polymeric materials such as processing aids, chemical stabilizers, compatibilizers e.g. where more than one polymer is used, fillers, and the like.

Absorbent core 86 suitably comprises hydrophilic fibers, such as a web or matt or loose collection of cellulosic fluff, in combination with a high-absorbency material commonly known as super-absorbent material. Absorbent core 86 preferably comprises a mixture of super-absorbent hydrogel-forming particles and wood pulp fluff. In place of the wood pulp fluff, one can use synthetic, polymeric, melt-blown fibers or a combination of melt-blown fibers and natural fibers. The super-absorbent material can be substantially homogeneously mixed with the hydrophilic fibers or can be otherwise combined into absorbent core 86.

Alternatively, absorbent core 86 can comprise a laminate of fibrous webs and super-absorbent material or other suitable means of maintaining a super-absorbent material in a localized area. Absorbent core 86 can additionally comprise an un-creped through air dried paper web material known as UCTAD.

Absorbent core 86 can have any of a number of shapes. For example and without limitation, absorbent core 86 can be rectangular, I-shaped or T-shaped. In such products as e.g. diaper-like articles, pull-on pants, and the like, absorbent core 86 is preferably narrower in the crotch portion than in the rear portion or the front portion, especially where the crotch portion of the personal care article is narrower than the rear portion or the front portion.

The high-absorbency material in absorbent core 86 can be selected from natural, synthetic and modified natural polymers and materials. The high absorbency material can be inorganic material, such as silica gels, or organic compounds, such as cross-linked polymers. The high absorbency material refers to any structure or composition, along with associated process, which renders normally water-soluble material substantially water insoluble but swellable, whereby absorbent properties are available but the swelled material is substantially immobile after absorbing water-based liquid. Such super-absorbent material can be fabricated by creating e.g. physical entanglement, crystalline domains, covalent bonds, ionic complexes and associations, hydrophilic associations such as hydrogen bonding, and hydrophobic associations, or Van der Waals forces. Two such super-absorbents are DRYTECH® 2035 M and FAVOR® SXM 880. DRYTECH® available from the Dow Chemical Company, Midland, Mich. FAVOR® is available from Stockhausen, Inc., Greensboro, N.C.

Personal care articles of the invention can be used in at least two different ways. First, personal care absorbent article 80 of FIG. 4, as shipped to the customer, can be used as a pant-type structure. In such format, first and second fasteners 98, 99, respectively, are, and remain, attached separately to landing zone 97 of front portion 81. The pant-type structure is slipped onto the wearer while retaining attachment of first and second fasteners 98, 99 to landing zone 97 of personal care absorbent article 80 through a cooperative engagement relationship.

Accordingly, the legs of the wearer are inserted through waist opening 91, and through leg openings 87. The pull-on pant is then pulled in a cephalic direction until leg openings 87 are snugly positioned at the groin of the wearer. The wearer can adjust the fitting of the pant-type structure to create a better relative positioning of the waist portion of the respective personal care article about the torso of the wearer, directed toward comfort of the wearer, thus to improve the fit.

Further adjusting to obtain a tighter or looser fit can be accomplished by the user by subsequent grasping and pulling of first and/or second fasteners 98, 99, of first and second lateral sections 93, 95, respectively, away from landing zone 97, thereby to disengage first and/or second fasteners 98, 99 from landing zone 97. Respective fasteners 98, 99, are then moved over desired location on landing zone 97, thus increasing or decreasing relative tension of elastic elements 18 associated with lateral sections 93, 95, and re-engaged to landing zone 97, so as to achieve the desired relationship between adjusted size of personal care absorbent article 80 and size of the wearer. Release and refastening of fasteners 98, 99 can occur multiple times (e.g. an indeterminate number of times) to enable proper fitting throughout the expected use life of the personal care article. Fasteners 98, 99 of first and second lateral sections 93, 95 can be adjusted individually or in combination with each other to create a relatively tighter or relatively looser fit.

Preferably, and as a user convenience, personal care articles of the invention are packaged having first and second fasteners 98, 99, cooperatively affixed in an engagement relationship with landing zone 97, whereby personal care articles of the invention can be put on a wearer in a similar fashion to that of conventional pull-on pants.

The second method of using personal care absorbent article 80 of FIG. 4 is to use such article as a diaper-like article. Before putting the diaper-like article on the prospective wearer, first and second fasteners 98, 99 are separated from landing zone 97 of personal care absorbent article 80, and front portion 81 is pulled away from rear portion 82. In the method of using such article as a diaper-like article, the separation of first and second fasteners 98, 99 from landing zone 97 can be performed before packaging by the manufacturer, or can be performed anytime prior to or during use by the user. After fasteners 98, 99 are separated from landing zone 97, the personal care article is laid on a preferably horizontal surface with bodyside liner 85 facing upwardly. The dorsocaudal portion of the torso of the wearer (e.g. infant or adult) is then laid or otherwise moved onto rear portion 82 of the personal care article. Front portion 81 is then brought frontwardly between the legs of the wearer and onto the torso of the wearer. First and second fasteners 98, 99 are fastened to landing zone 97, completing the application of the personal care article onto the wearer. Those skilled in the art will recognize the instant above description as a known method of putting a diaper-like article on a wearer.

Alternative methods of putting on a diaper-like article will be obvious to those of ordinary skill in the art. Such alternative methods include, but are not limited to, e.g. putting the diaper-like article on a wearer when such wearer is in a position other than lying down, e.g. standing, and/or when such wearer's slacks/pants are not entirely removed, but rather, lowered to expose the lower trunk and groin region of the wearer.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

Having thus described the invention, what is claimed is:

1. A method of fabricating a web suitable for use in making a personal care absorbent article, the method comprising:
   (a) fabricating a resiliently extensible web by bringing together and securing to each other (i) web substrate elements, and (ii) resiliently stretchable elastic elements in stretched condition, the securement between the elastic elements and the web substrate elements being defined by alternating zones of securement and non-securement of the elastic elements to at least one of the web substrate elements along a length of the web substrate;
   (b) deactivating elastic elements in the non-securement zones thereby (i) to attenuate resilient retraction of the web in such non-securement zones in response to activity of the elastics and correspondingly (ii) to distinguish the securement zones as relatively more resiliently stretchable and the non-securement zones as relatively less resiliently stretchable;
   (c) applying, to the relatively non-stretchable non-securement zones, patches of mechanical fastener material extending generally between respective adjacent ones of the relatively more resiliently stretchable securement zones;
   (d) fabricating a plurality of workpieces from the web, each workpiece defining a respective free end having a respective patch of the mechanical fastener material;
   (e) separating each of the workpieces from the web, each workpiece defining an opposing end opposing the respective free end, each opposing end defining a second respective patch of the mechanical fastener material;
   (f) arranging the workpieces in end-to-end relationship with intervening elements; and
   (g) releasably attaching the respective patches of the mechanical fastener material on the workpieces to hook respective receptive areas on the intervening elements to releasably attach the workpieces to the intervening elements in fabricating a length of the extensible web.

2. A method as in claim 1 wherein the releasable attachment of the workpieces to the intervening elements comprises the only attachment between the workpieces and the intervening elements.

3. A method as in claim 1, the method comprising developing an alternating arrangement of the workpieces and the intervening elements such that each such workpiece is between two such intervening elements and each such intervening element is between two such workpieces.

4. A method as in claim 1, including deactivating elastic elements in the non-securement zones by cutting such elastic elements.

5. A method as in claim 1, including deactivating elastic elements in the non-securement zones by applying ultrasonic energy to such elastic elements through an intervening layer.

6. A method of fabricating a web suitable for use in making a personal care absorbent article, the method comprising:
   (a) fabricating a resiliently extensible web by bringing together and securing to each other (i) web substrate elements, and (ii) resiliently stretchable elastic elements in stretched condition, the securement between the elastic elements and the web substrate elements being defined by alternating zones of securement and non-securement of the elastic elements to at least one of the web substrate elements along a length of the web substrate;
   (b) deactivating the elastic elements in the non-securement zones to attenuate resilient retraction of the web in such non-securement zones such that the securement zones are relatively more resiliently stretchable than the non-securement zones;
   (c) applying patches of fastener material to the non-securement zones extending between respective adjacent ones of the securement zones;
   (d) defining a first end of a workpiece by disposing a respective patch of the fastener material on a free end of the web;
   (e) separating the workpiece from the web to define a second end of the workpiece;
   (f) disposing a second respective patch of the fastener material on the second end of the workpiece;
   (g) providing a plurality of workpieces as in step (f);
   (g) arranging the workpieces adjacent a plurality of intervening elements, respective ones of the intervening elements defining respective receptive surface areas;
   (i) releasably attaching the fastener material on the workpieces to the receptive surface areas to releasably attach the workpieces and the intervening elements to each other in fabricating a length of the extensible web.

7. The method as in claim 6, further comprising the step alternately arranging the workpieces and the intervening elements.

8. The method as in claim 6, further comprising the step of deactivating the elastic elements in the non-securement zones by one of mechanically cutting such elastic elements, by applying ultrasonic energy to such elastic elements through an intervening layer, and by heating such elastic elements through the intervening layer.

* * * * *

UNITED STATES PATENT AND TRADEMARK OFFICE
CERTIFICATE OF CORRECTION

PATENT NO. : 6,712,922 B2  
DATED : March 30, 2004  
INVENTOR(S) : Jesse Paul Sorenson et al.

It is certified that error appears in the above-identified patent and that said Letters Patent is hereby corrected as shown below:

<u>Title page,</u>
Item [75], Inventors, please add the following:

-- Suzanne Marie Schmoker
4212 Brooks Road
Oshkosh, WI 54904 --

Signed and Sealed this

Seventh Day of September, 2004

JON W. DUDAS
*Director of the United States Patent and Trademark Office*